US00PP33496P2

(12) United States Plant Patent
Kraan

(10) Patent No.: US PP33,496 P2
(45) Date of Patent: Sep. 21, 2021

(54) ***HYDRANGEA* PLANT NAMED 'BOKOMAHO'**

(50) Latin Name: *Hydrangea paniculata*
Varietal Denomination: Bokomaho

(71) Applicant: Kees Jan Kraan, Alphen aan den Rijn (NL)

(72) Inventor: Kees Jan Kraan, Alphen aan den Rijn (NL)

(73) Assignees: Boot & Co Boomkwekerijen BV, Boskoop (NL), part interest; Kolster BV, Boskoop (NL), part interest ( * ) Notice: Subject to any disclaimer, the term of this patent is extended or adjusted under 35 U.S.C. 154(b) by 0 days.

(21) Appl. No.: 17/082,113

(22) Filed: Oct. 28, 2020

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

(56) References Cited

PUBLICATIONS

PLUTO Plant Variety Database p. 1. Mar. 9, 2021.*

* cited by examiner

*Primary Examiner* — Annette H Para
(74) *Attorney, Agent, or Firm* — Penny J. Aguirre

(57) ABSTRACT

A new cultivar of *Hydrangea paniculata* plant named 'Bokomaho' that is characterized by its very compact plant habit, its strong and healthy foliage that stays healthy during flowering, its dense, ovate to conical shaped inflorescences, its inflorescences that consist of fertile and sterile flowers, and its sterile flowers with sepals that are white in color that change to yellow-green in color.

2 Drawing Sheets

Botanical classification: *Hydrangea paniculata.*
Varietal denomination: 'Bokomaho'.

BACKGROUND OF THE INVENTION

The present invention relates to a new and distinct cultivar of *Hydrangea paniculata* and will be referred to hereafter by its cultivar name, 'Bokomaho'. 'Bokomaho' represents a new *Hydrangea*, a perennial shrub grown for landscape use and as a potted plant.

'Bokomaho' was derived from a breeding program conducted by the Inventor at a nursery in Boskoop, The Netherlands. The objective of the breeding program is to select new cultivars of *Hydrangea* with dense and compact plant habits, dense paniculate inflorescences and unique inflorescence shapes.

The new cultivar arose from open pollination in August of 2012 of *Hydrangea paniculata* 'DVPPinky' (U.S. Plant Pat. No. 16,166). The male parent is therefore unknown. 'Bokomaho' was selected as a single unique plant in August of 2018 from amongst the resulting seedlings.

Asexual propagation of the new cultivar was first accomplished by softwood stem cuttings by the Inventor in August of 2016 in Boskoop, The Netherlands (and further evaluated before selection). Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bokomaho' as a unique cultivar of *Hydrangea.*

1. 'Bokomaho' exhibits a very compact plant habit.
2. 'Bokomaho' exhibits strong and healthy foliage that stays healthy during flowering.
3. 'Bokomaho' exhibits dense, ovate to conical shaped inflorescences.
4. 'Bokomaho' exhibits inflorescences that consist of fertile and sterile flowers.
5. 'Bokomaho' exhibits sterile flowers with sepals that are white in color that change to yellow-green in color.

The seed parent of 'Bokomaho' differs from 'Bokomaho' in having a less compact plant habit growing to an average height of 2 m, inflorescences that are larger in size and conical shape, and sterile flower sepals that change to a deep pink-red color. 'Bokomaho' can be compared to the *Hydrangea paniculata* cultivars 'Jane' (U.S. Plant Pat. No. 22,330) and 'Limelight' (U.S. Plant Pat. No. 12,874). 'Jane' is similar to 'Bokomaho' in overall plant shape and inflorescence shape. 'Jane' differs from 'Bokomaho' in having inflorescences that are more broadly ovate in shape, sterile flower sepals that are green-white to lime colored that change to pink-red in color. 'Limelight' is similar to 'Bokomaho' in overall plant shape. 'Limelight' differs from 'Bokomaho' in having a less compact plant habit; growing to an average height of 2.5 m, inflorescences that are more broadly ovate in shape, sterile flower sepals that are green-white to lime in color that change to pink in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by RHS Gardening, Plantentuin Esveld, and Hornbach.

BRIEF DESCRIPTION OF THE DRAWINGS

The accompanying colored photographs illustrate the overall appearance and distinct characteristics of the new *Hydrangea*. The photographs were taken of a two-year-old plant of 'Bokomaho' as field grown outdoors in Boskoop, The Netherlands.

The photograph in FIG. 1 provides a side view of the plant habit of 'Bokomaho' in bloom.

Figure 1:
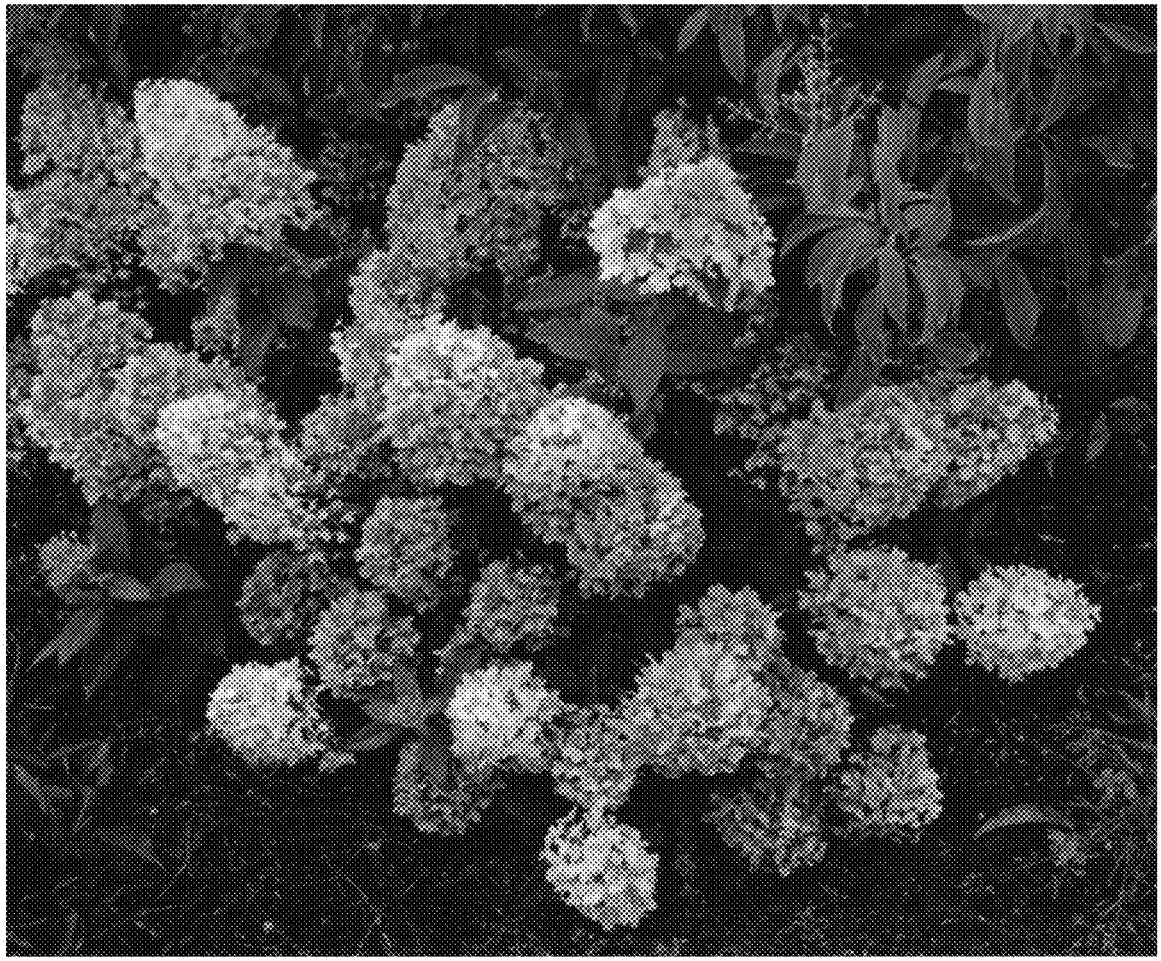
Figure 2:
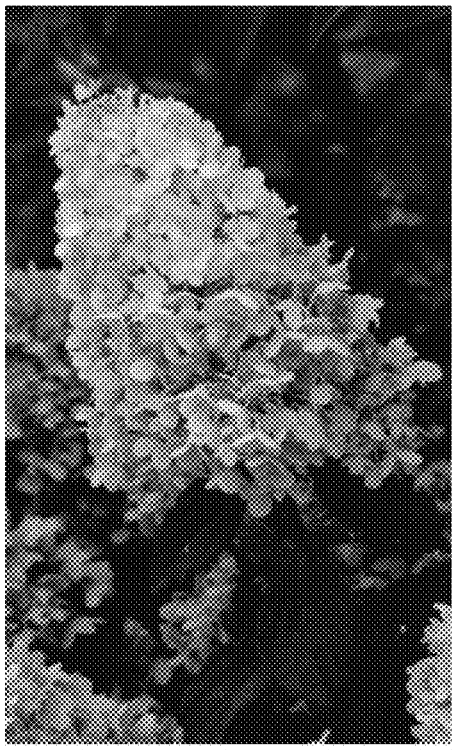

The photograph in FIG. 2 provides a close-up view of an inflorescence of 'Bokomaho'.

Figure 3:
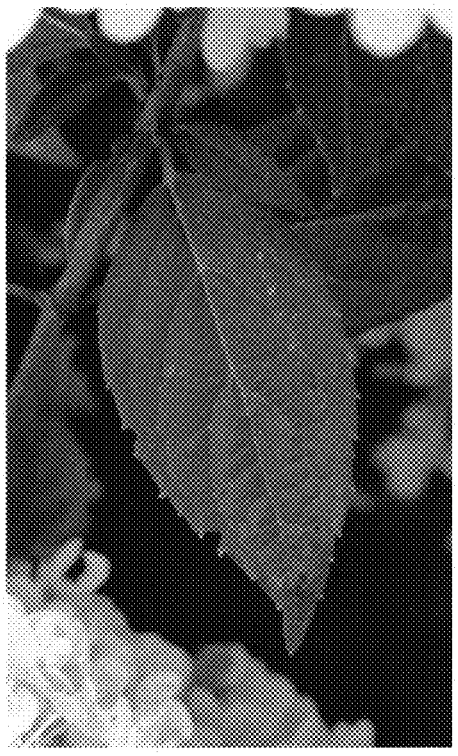

The photograph in FIG. 3 provides a close-up view of the foliage of 'Bokomaho'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Bokomaho' as field grown in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period.*—Approximately 6 weeks from midsummer into early fall in The Netherlands.
- *Plant type.*—Deciduous shrub, panicle type *Hydrangea.*
- *Plant habit.*—Very compact, globular and upright spreading.
- *Height and spread.*—Average of 51.6 cm in height, 54.3 cm in spread, fully mature plant reaches 150 cm in height, 100 cm in spread.
- *Hardiness.*—At least in U.S.D.A. Zones 5 to 9.
- *Diseases and pests.*—No susceptibility and resistance to diseases or pests has been observed.
- *Root description.*—Fine, fibrous and dense, NN155A and 164A in color.
- *Propagation.*—Softwood stem cuttings.
- *Root development.*—An average of 30 days for root initiation with a finished plant produced in an average of 12 months.
- *Growth rate and vigor.*—Low to moderate.

Stem description:

- *Stem shape.*—Rounded.
- *Stem strength.*—Strong.
- *Stem color.*—Young; 146B to 146C, mature; 199A, bark; 199B and N199B.
- *Stem size.*—Average of 27 cm in length (excluding inflorescence) and 4 mm in diameter.
- *Stem surface.*—Moderately covered with lenticels; an average of 1.25 mm in length and 0.75 mm in diameter, 164C in color.
- *Stem aspect.*—Upright, average angle of 40° to vertical.
- *Internode length.*—An average of 3.9 cm.
- *Branching.*—Freely branching with an average of 26 lateral branches.

Foliage description:

- *Leaf shape.*—Narrowly ovate to narrowly elliptic.
- *Leaf arrangement.*—Opposite or in whorls of three.
- *Leaf division.*—Simple.
- *Leaf base.*—Short attenuate.
- *Leaf apex.*—Apiculate to acute.
- *Leaf margins.*—Serrate.
- *Leaf venation.*—Pinnate, color; upper surface 146B, lower surface 146C to 146D.
- *Leaf size.*—An average of 7.8 cm in length and 3.4 cm in width.
- *Leaf attachment.*—Petiolate.
- *Leaf number.*—An average of 16 per lateral stem.
- *Leaf surface.*—Both surfaces sparsely pubescent with very short adpressed strigose hairs; an average of 0.5 mm in length, color too small and too sparsely present to be measured.
- *Leaf color.*—Young upper surface; 143A, young lower surface; 146B, mature upper surface; NN137A, mature lower surface; 147B.
- *Petioles.*—An average of 1.8 cm in length and 1.75 mm in diameter, upper surface 152A, margins 174A in color, lower surface 195A in color, slightly glossy, sparsely to moderately covered with very short hairs; average length 0.3 mm, color too small and too sparsely present to be measured.

Inflorescence description:

- *Inflorescence type.*—Paniculate, ovate to conical in shape, comprised of sterile flowers and fertile flowers.
- *Lastingness of inflorescence.*—Sterile flowers; persistent for an average of 6 weeks, fertile flowers; self-cleaning, an average of 5 days.
- *Inflorescence number.*—One per lateral stem.
- *Inflorescence size.*—An average of 14.5 cm in height and 12.5 cm in diameter.
- *Flower number.*—An average of 600 sterile flowers and 375 fertile flowers per panicle.
- *Flower fragrance.*—Moderate, sweet and pleasant.
- *Flower aspect.*—Sterile flowers; upright to outward, fertile flowers; upright.
- *Flower size.*—Sterile flowers; average of 2.2 cm in diameter and 7 mm in depth, fertile flowers; an average of 7 mm in diameter and in depth.
- *Flower type.*—Sterile flowers; rotate, fertile flowers; rotate, petals drop when mature.
- *Flower buds.*—Sterile flowers; an average of 5 mm in length and 6.5 mm in diameter, cup-shaped, 145C in color, fertile flowers; an average of 3 mm in length and 2.5 mm in diameter, obovate in shape, 157D in color, immature calyx 193A in color.
- *Peduncles.*—Average of 12.9 cm in length, 2.5 mm in diameter, main peduncle held in a straight vertical angle, lateral peduncles held in an average angle of 45°, moderately strong, 146B to 146C in color, surface is matte and moderately covered with a thin pubescence, hairs up to 0.4 mm in length and too small to measure color, surface also moderately covered with lenticels; average of 1 mm in length and 0.5 mm in diameter, 157A in color.

*Pedicels.*—Sterile flowers; moderate strength, an average of 1.4 cm in length and 1 mm in width, NN155D in color, held in an average angle of 25° to main peduncle, surface is matte, sparsely covered with thin pubescence; average of 0.4 mm in length, NN155D in color, fertile flowers; moderate strength, an average of 5 mm in length, 0.5 mm in diameter, held in an average angle of 20°, 145D in color, surface is matte, sparsely to moderately covered with a thin pubescence; average of 0.3 mm in length, 145C in color.

*Petals.*—Sterile flowers; 4 to 5 per flower, rotate, ovate to concave in shape, acute apex, cuneate base, entire margins, 2 mm in length, 1 mm in width, upper surface glabrous and slightly glossy, lower surface glabrous and matte, color when opening and fully open upper surface NN155D, color when opening and fully open lower surface NN155B, fertile flowers; average of 5, rotate, strongly reflexed, ovate to slightly concave in shape, acute apex, cuneate base, entire margins, 2.5 mm in length and 1.25 mm in width, upper surface is glabrous and slightly glossy, lower surface glabrous and matte, color when opening and fully open upper surface; NN155C, color when opening lower surface; NN155A, color when fully open lower surface NN155A.

*Sepals.*—Sterile flowers; 4 (occasionally 5), rotate, obovate to elliptic in shape, apex is obtuse, base is cuneate, entire margins, 1.1 cm in length, 8.5 mm in width, both surfaces glabrous and matte, color; when opening upper and lower surface 155A, when fully open upper surface NN155A, fading to 144B to 145A, when fully open lower surface 155B, fading to 145A, fertile flowers; average of 5, rotate, narrow deltoid in shape, acuminate apex, broadly cuneate base, entire margins, 0.75 mm in length and width, both surfaces glabrous and matte, color; when opening upper and lower surface 193A, when fully open upper and lower surface 150D.

Reproductive organs:

*Gynoecium.*—Sterile flowers; not produced, fertile flowers; 3 pistils, an average of 0.75 mm in length, stigma; club-shaped and 155C in color, style; 0.5 mm in length, 155C in color, ovary is 145D in color.

*Androecium.*—Sterile flowers; an average of 8 stamens, filaments; an average of 1.5 mm in length and NN155D in color, anthers; broad oblong in shape, an average of 0.5 mm in length and 155A in color, pollen; low in quantity and 155D in color, fertile flowers; an average of 10 stamens, filaments; an average of 3 mm in length and NN155C in color, anthers; broad oblong in shape, an average of 0.5 mm in length and 156C in color, pollen; moderate in quantity and 197B in color.

*Fruit and seed.*—None observed to date.

It is claimed:

1. A new and distinct cultivar of *Hydrangea* plant named 'Bokomaho' substantially as herein illustrated and described.

* * * * *